US00PP14243P29

(12) United States Plant Patent
Hanes

(10) Patent No.: US PP14,243 P2
(45) Date of Patent: Oct. 14, 2003

(54) PETUNIA PLANT NAMED 'JAM SCARL'

(50) Latin Name: *Petunia hybrida*
Varietal Denomination: 'Jam Scarl'

(75) Inventor: Mitchell Eugene Hanes, Morgan Hill, CA (US)

(73) Assignee: Goldsmith Seed Inc., Gilroy, CA (US)

( * ) Notice: Subject to any disclaimer, the term of this patent is extended or adjusted under 35 U.S.C. 154(b) by 0 days.

(21) Appl. No.: 10/389,220

(22) Filed: Mar. 13, 2003

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates P.C.

(57) ABSTRACT

A petunia cultivar particularly distinguished by scarlet colored flowers, compact habit and good basal branching.

1 Drawing Sheet

Genus and species: Petunia hybrida.
Variety denomination: 'Jam Scarl'.

BACKGROUND OF THE NEW PLANT

The present invention comprises a new and distinct cultivar of petunia, botanically known as Petunia hybrida, and hereinafter referred to by the cultivar name 'Jam Scarl'. The new cultivar is asexually reproduced from vegetative cuttings and tissue culture resulting from the cross of the seed/pod parent 'Red Horizon', seed propagated commercial line that is unpatented×99-220-17, a double purple proprietary line that is unnamed and unpatented.

'Jam Scarl' is a product of a planned breeding program intended to create new petunia plants with scarlet colored flowers, compact habit, good basal branching and moderately vigorous growth.

The new cultivar was created in 1999 in Gilroy, Calif. and has been asexually reproduced repeatedly by vegetative cuttings and tissue culture in Gilroy, Calif., Andijk, The Netherlands, and Guatemala over a two and half year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Jam Scarl'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light.

Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Petunia hybrida.
*Commercial.*—Petunia.
Form: Semi upright and decumbent.
Growth and branching habit: Good vigorous habit, well-branched, full plant.
Height: From soil level to top of blooms: Approximately 10–15 cm.
Width: Approximately 50–60 cm including flowers.
Time to produce a finished flowering plant: 9–11 weeks.
Outdoor plant performance: Full sun; free-flowering through the summer; some heat tolerance; Used as a hanging plant, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 3.8–4.3 cm.
Width: 2.0–3.2 cm.
Leaf blade shape: Ovate/Elliptic.
Leaf margin: Entire.
Apex aspect: Acute.
Base aspect: Acuminate.
Leaf color: Upper side; RHS 137A (green); Underside; RHS 137C (green).
Texture: Sparse short glandular hairs.
Venation: Palmate.
Venation color: RHS 144A/B (yellow-green).
Petiole length: 0.9–1.5 cm.
Petiole width: 0.2–0.3 cm.
Petiole color: RHS 144A/B (yellow-green).
Petiole texture: Sparse long glandular hairs.

THE STEM

Length: 45–55 cm.
Diameter: 0.4–0.5 cm.
Internode length: 1.0–3.5 cm.
Color: RHS 144A (yellow-green).
Texture: Sparse long glandular hairs.
Stem anthocyanin: None.
Peduncle color: Close to RHS 144A (yellow-green).
Peduncle length: 3.0–3.4 cm.
Peduncle diameter: 0.15–0.2 cm.
Peduncle texture: Many glandular hairs of various sizes.

THE BUD

Shape: Oblong.
Diameter: 0.5 cm.
Length: 1.5–2.6 cm.
Color at tight bud: RHS 151C (yellow-green) & RHS 152A (yellow-green).

THE FLOWER

Blooming habit: Continuous all through the growing season. Good floriferousness.
Young flower color: Front side; close to RHS 45A (red); RHS 183A (greyed-purple) mid-veins.
Young flower floret diameter: 4.7–5.1 cm.
Mature flower color: Front side, close to RHS 45B (red); RHS 183A (greyed-purple) mid-veins; RHS 183D (greyed-purple) faint secondary veins. Underside, shades of RHS 43C (red) at petal margin to RHS 39C (red) at the corolla; RHS 177C (greyed-orange) mid-veins; RHS 174C (greyed-orange) secondary veins.
Corolla tube color inside: RHS 159C (orange-white) base color; RHS 166A (greyed-orange) mid-veins; RHS 165A (greyed-orange) & RHS 166B (greyed-orange) secondary veins covering much of corolla.
Corolla tube length: 2.7–3.0 cm.
Corolla outside texture: Many glandular hairs of various sizes.
Floret form and number of petals: Funnel form, 5 lobed petals (single type) fused at base.
Flower (limb) diameter: 5.0–5.5 cm.
Petal apex shape: Cuspidate.
Petal base shape: Fused.
Petal margin: Entire.
Waviness of petals: Very weak.
Petal libation: Moderate.
Petal texture: Papillose.
Sepals: 5.
Sepal color: RHS 137A (green).
Sepal length: 2.1–2.2-cm.
Sepal width: 0.5–0.7 cm.
Sepal shape: Oblong.
Sepal apex: Acute.
Sepal texture: Many glandular hairs of various sizes.
Lastingness of individual blooms: 4–8 days.
Fragrance: None.

THE REPRODUCTIVE ORGANS

Stamens: Five, 2 taller and 3 shorter.
Filament color: RHS N155B (white).
Pollen color: RHS 158A (yellow-white).
Pistil: One.
Stigma: RHS 145A (yellow-green) center spot of RHS 143B (green).
Style color: RHS 145B/C (yellow-green).
Fruit seed set: Not observed.

DISEASE AND INSECT RESISTANCE

Not observed.

COMPARISON WITH KNOWN CULTIVARS

Compared to its female parent ‘Red Horizon’ as follows: The female parent has a larger flower and the plant is more upright than the plant of the ‘Jam Scarl’.

Compared to its male parent 99-220-17 as follows: The male parent has a double flower that is purple compared to the single scarlet flower of ‘Jam Scarl’. The male parent also grows upright as compared to the more trailing growth of the ‘Jam Scarl’.

I claim:

1. A new and distinct petunia plant as shown and described herein.

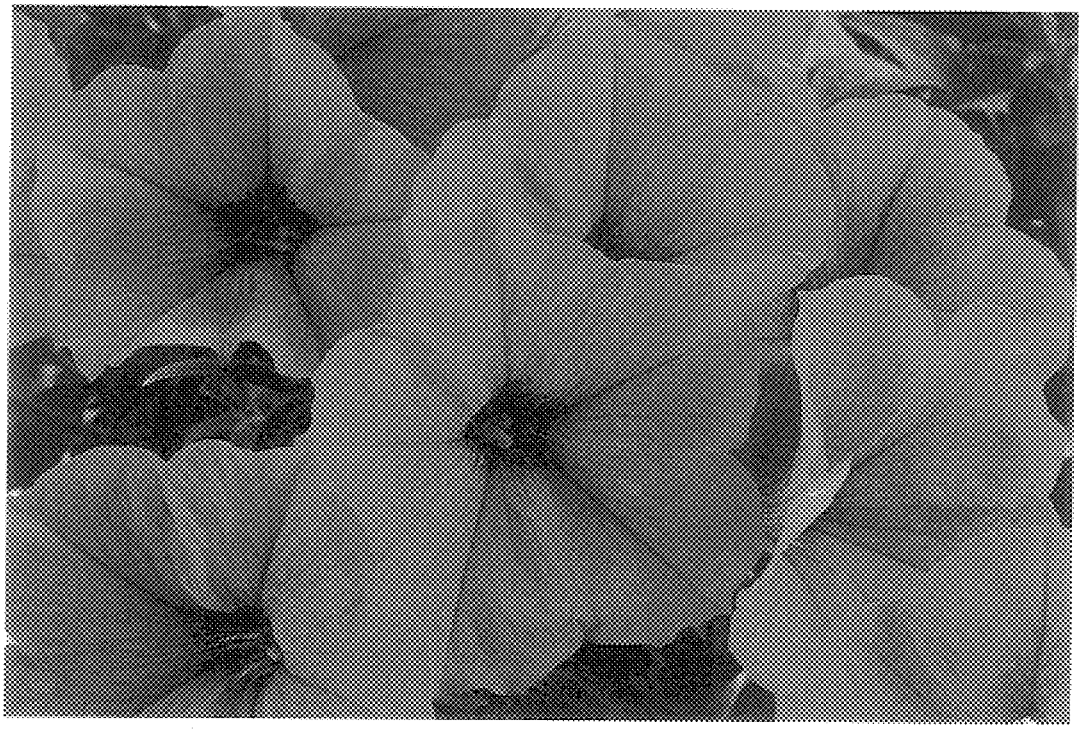

* * * * *